(12) United States Patent
Kang et al.

(10) Patent No.: US 12,102,612 B2
(45) Date of Patent: Oct. 1, 2024

(54) PHARMACEUTICAL COMPOSITION COMPRISING HYDROQUINONE DERIVATIVE FOR PREVENTING OR TREATING OBESITY OR NONALCOHOLIC STEATOHEPATITIS

(71) Applicant: BIOTOXTECH CO., LTD., Cheongju-si (KR)

(72) Inventors: Jong Koo Kang, Cheongju-si (KR); Suk Mo Kang, Cheongju-si (KR); Heung Mo Bae, Cheongju-si (KR)

(73) Assignee: BIOTOXTECH CO., LTD., Cheongju-si (KR)

( * ) Notice: Subject to any disclaimer, the term of this patent is extended or adjusted under 35 U.S.C. 154(b) by 736 days.

(21) Appl. No.: 17/288,696

(22) PCT Filed: Sep. 9, 2019

(86) PCT No.: PCT/KR2019/011664
§ 371 (c)(1),
(2) Date: Apr. 26, 2021

(87) PCT Pub. No.: WO2020/085644
PCT Pub. Date: Apr. 30, 2020

(65) Prior Publication Data
US 2021/0393566 A1 Dec. 23, 2021

(30) Foreign Application Priority Data
Oct. 25, 2018 (KR) .................. 10-2018-0128434

(51) Int. Cl.
*A61P 1/16* (2006.01)
*A61K 31/085* (2006.01)
*A61K 31/235* (2006.01)

(52) U.S. Cl.
CPC .......... *A61K 31/235* (2013.01); *A61K 31/085* (2013.01); *A61P 1/16* (2018.01)

(58) Field of Classification Search
CPC ........ A61P 1/16; A61K 31/085; A61K 31/235
See application file for complete search history.

(56) References Cited

U.S. PATENT DOCUMENTS 7,847,132 B2   12/2010   Ishikawa et al.

FOREIGN PATENT DOCUMENTS

| JP | 107-258132 A | 10/1995 |
| JP | H08-067627 A | 3/1996 |
| JP | 2009-256226 A | 11/2009 |
| KR | 10-1042697 B1 | 6/2011 |
| KR | 10-2014-0120639 A | 10/2014 |
| KR | 10-2013574 B1 | 8/2019 |

OTHER PUBLICATIONS

Hirose et al. Chemoprevention of heterocyclic amine-induced carcinogenesis by phenolic compounds in rats . . . , Cancer Letters 143 (1999), p. 173-178 (Year: 1999).*
Chen et al. Micronutrient Antioxidants and Nonalcoholic Fatty Liver Disease, Int. J. Mol. Sci. 2016, 17, 1379, p. 1-16 (Year: 2016).*
International Search Report issued for International Application No. PCT/KR2019/011664 on Dec. 9, 2019, 4 pages.

\* cited by examiner

*Primary Examiner* — Kortney L. Klinkel
*Assistant Examiner* — Richard Grant Peckham
(74) *Attorney, Agent, or Firm* — ROTHWELL, FIGG, ERNST & MANBECK, P.C.

(57) ABSTRACT

The present invention relates to a pharmaceutical composition comprising a hydroquinone derivative of general formula 1 as an active ingredient. The pharmaceutical composition has the effects of: enabling the prevention or treatment of obesity by inhibiting weight gain and visceral fat accumulation; and enabling the prevention or treatment of nonalcoholic steatohepatitis by inhibiting fat accumulation in liver tissue and lobular inflammation, and by improving insulin resistance.

1 Claim, 9 Drawing Sheets

PHARMACEUTICAL COMPOSITION COMPRISING HYDROQUINONE DERIVATIVE FOR PREVENTING OR TREATING OBESITY OR NONALCOHOLIC STEATOHEPATITIS

CROSS REFERENCE TO RELATED APPLICATION(S)

This application is a 35 U.S.C. 371 National Phase Entry Application from PCT/KR2019/011664, filed on Sep. 9, 2019 and designating the United States, which claims priority based on Korean Patent Application No. 10-2018-0128434 filed on Oct. 25, 2018, the disclosures of which are incorporated herein by reference in their entirety.

TECHNICAL FIELD

The present invention relates to a pharmaceutical composition comprising a hydroquinone derivative for prevention or treatment of obesity or non-alcoholic steatohepatitis.

BACKGROUND ART

Obesity is a condition in which excess body fat has accumulated due to imbalance between energy intake and consumption to an extent that adipose tissues are abnormally increased. Obesity is classified into simple obesity, which is due to excessive caloric intake and a lack of physical activity without special causative disease, and symptomatic obesity, which is secondarily caused by genetic factors, endocrine diseases, an improper action of the appestat, and side effects of drugs. Simple obesity accounts for about 95% of all of obesity cases.

Obesity is recognized more seriously because of various complications that can be caused by obesity rather than its own risk. Obesity is known to increase the risk of metabolic syndrome such as hypertension, hyperlipidemia, and diabetes, fatty liver, joint abnormalities, and cancer.

Representative among commercially available therapeutics for obesity are Xenical™ (Roche), which has Orlistat as a main ingredient, and Reductil™ (Abbott), which has sibutramine as a main ingredient. These medicines exhibit side effects such as nausea, diarrhea, abdominal pain, insomnia, increased blood pressure, fatty liver, etc. Therefore, there is a need to develop a safe therapeutic for obesity with few side effects.

With the increase of the obese population, the prevalence of metabolic syndrome has recently increased, together with the prevalence of non-alcoholic fatty liver disease. It is reported that fatty liver is induced as a complication of obesity, as described above. Other various factors including, for example, alcohol use, diabetes, malnutrition, drug abuse, etc. are also reported to cause fatty liver. Fatty liver is defined as a condition where more than 5% of the liver is accounted for by fat build-up, as measured by a biopsy. "Non-alcoholic fatty liver disease" (NAFLD) is the term for a range of conditions caused by a build-up of fat in the liver, as measured by radiography or biopsy, without clear cause such as alcohol use, drug intake leading to fatty liver, liver diseases attributed to other accompanying factors, etc. NAFLD encompasses simple steatosis and nonalcoholic steatohepatitis, (NASH). Simple fatty liver has a relatively good prognosis while NASH is present in 10-20% of patients with NAFLD and exhibits liver inflammation leading to a hepatocytic damage, together with a build-up of fat in the liver. NASH is a fatal disease in that 9-25% of patients with NASH progress to liver cirrhosis, which leads to a death in 30-40% of the cirrhosis cases due to complications of liver diseases.

NASH is closely correlated with metabolic syndrome such as obesity and insulin resistance, but the exact pathology and therapies remain unknown. Diagnosis of NASH is mainly performed through histopathological examination. Minimally essential findings for diagnosis of NASH include steatosis, ballooning degeneration of hepatocytes, and inflammation in hepatic lobules. For effectively treating NASH, it is particularly important to inhibit progression from nonalcoholic fatty liver to steatohepatitis and from steatohepatitis to a next step by reducing the inflammation of steatohepatitis. Moreover, a reduction in the insulin resistance and visceral fat accumulation associated with NASH by kinesiotherapy or drug treatment is a management objective very important for treating NASH.

With the increase of social costs for NASH, many researchers have tried to develop a cure, but up to date, there has been no drug treatment that has been clinically proven for NASH. Particularly, no therapeutics have been developed for preventing the onset or progression of NASH. There are no therapeutics developed that have been approved as a cure for NASH. There are only off-label drugs as the best alternative plan in consideration of safety and efficacy for patients. Insulin resistance modifiers (e.g. peroxisome proliferator-activated receptors (PPARs) agonists or farnesoid X receptor (FXR) agonists) are under clinical development, but none have been proven effective. Some drugs cause side effects, such as dyslipidemia. In many cases, general antioxidative and anti-inflammatory efficacies alone fail to exert sufficient therapeutic efficacy in actual animal tests and clinical trials for NASH because many pathophysiological factors are involved in NASH.

It is disclosed that specific hydroquinone derivatives have inhibitory effects on hepatic fibrosis in carbon tetrachloride (CCL4)-induced cirrhosis model, and exhibit an effect of improving a liver function in acetaminophen- and α-naphthylisothiocyanate (ANIT)-induced acute liver injury model (Japanese Patent No. 1996-67627 A and Korean Patent No. 10-1042697). However, reports on whether the hydroquinone derivatives disclosed in the prior art documents have direct efficacies against obesity, non-alcoholic fatty liver, or NASH were not found anywhere in the prior art documents nor in other documents.

Leading to the present invention, thorough and intensive research, conducted by the present inventors, resulted in the finding that the hydroquinone derivatives exhibit combined alleviative effects on risk factors of NASH, such as obesity, visceral fat accumulation, or insulin resistance as well as on histopathological fat accumulation in liver tissues and inflammation in hepatic lobules, thereby having an efficacy for the prevention or treatment of NASH.

DETAILED DESCRIPTION OF THE INVENTION

Technical Problem

A purpose of the present invention is to provide a pharmaceutical composition comprising a hydroquinone derivative for prevention or treatment of obesity or NASH.

Technical Solution

The present invention relates to a pharmaceutical composition comprising a hydroquinone derivative of General Formula 1 as an active ingredient for prevention or treatment of obesity or NASH.

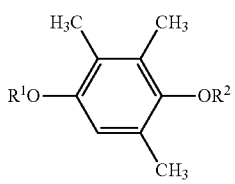

[General Formula 1]

wherein $R^1$ is an alkyl of 4-8 carbon atoms, and $R^2$ is a hydrogen atom, an alkyl carbonyl of 2-6 carbon atoms, or an alkoxy carbonyl of 2-6 carbon atoms.

In the pharmaceutical composition, the hydroquinone derivative of General Formula 1 is preferably 2,3,5-trimethylhydroquinone-1-hexylether (compound 1) or 2,3,5-trimethylhydroquinone-1-hexylether-4-acetate (compound 2).

In the pharmaceutical composition, the NASH is preferably obese NASH.

Another aspect of the present invention pertains to a food comprising the hydroquinone derivative of General Formula 1 as an active ingredient for prevention or alleviation of obesity or NASH.

In the food composition, the hydroquinone derivative of General Formula 1 is preferably 2,3,5-trimethylhydroquinone-1-hexylether (compound 1) or 2,3,5-trimethylhydroquinone-1-hexylether-4-acetate (compound 2).

In the food composition, NASH is preferably obese NASH.

Below, a detailed description will be given of the present invention.

The present invention relates to a pharmaceutical composition comprising a hydroquinone derivative of General Formula 1 as an active ingredient for prevention or treatment of obesity or NASH:

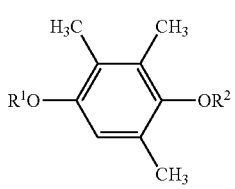

[General Formula 1]

wherein $R^1$ is an alkyl of 4-8 carbon atoms, and $R^2$ is a hydrogen atom, an alkyl carbonyl of 2-6 carbon atoms, or an alkoxy carbonyl of 2-6 carbon atoms.

The alkyl of 4-8 carbon atoms for $R^1$ may be a straight, a branch, or a circular type, and examples thereof include various butyl groups, various pentyl groups, various hexyl groups, various heptyl groups, various octyl groups, a cyclobutyl group, a cyclopentyl group, a cyclohexyl group, a cycloheptyl group, and a cyclooctyl group. The alkyl group may be preferably a straight alkyl of 4-7 carbon atoms, with greater preference for n-hexyl.

In addition, the alkylcarbonyl of 2-6 carbon atoms for $R^2$ may be a straight type or a branched type, as exemplified by acetyl, propionyl, butyryl, and isobutyryl. In addition, the alkoxycarbonyl of 2-6 carbon atoms for $R^2$ may be a straight type or a branched type, as exemplified by methoxycarbonyl, ethoxycarbonyl, propoxycarbonyl, and isopropoxycarbonyl.

In the pharmaceutical composition, the hydroquinone derivative of General Formula 1 is preferably 2,3,5-trimethylhydroquinone-1-hexylether or 2,3,5-trimethylhydroquinone-1-hexylether-4-acetate.

The pharmaceutical composition according to the present invention has prophylactic, alleviative, or therapeutic effects on obesity by inhibiting weight gain or visceral fat accumulation.

In addition, the present invention shows prophylactic, alleviative, or therapeutic effects on NASH by reducing insulin resistance as well as by inhibiting fat accumulation in hepatic tissues and lobular inflammation. The present invention is applicable to the treatment of histopathological traits of NASH, that is, the treatment of all types of NASH characterized by steatosis, ballooning degeneration of hepatocytes, and lobular inflammation, and preferably the treatment of obese NASH.

The hydroquinone derivative of General Formula 1 was identified to be a highly safe compound. Particularly, 2,3,5-trimethylhydroquinone-1-hexylether was proven to be a highly safe compound as no abnormal responses were observed even at a single dose of up to 2,000 mg per adult and at a dose of up to 1,000 mg per adult for repetitive administration for 14 days. Thus, the composition of the present invention can be advantageously used for treating obesity or NASH, which are chronic and need a long-term care.

The pharmaceutical composition of the present invention may be administered orally or parenterally, with preference for oral administration.

A suitable dose of the pharmaceutical composition of the present invention may vary depending on various factors including pharmaceutical formulation methods, administration methods, the patient's age, body weight, sex, severity of diseases, diet, administration time, administration route, excretion rate, and sensitivity to a used pharmaceutical composition. For parenteral administration, a daily dose of the hydroquinone derivative described above is generally in the range of about 0.01-100 mg/kg body weight and preferably in the range of about 0.05-50 mg/kg body weight. In addition, the dose of the hydroquinone derivative for oral administration ranges from about 0.1 to 500 mg/kg body weight and preferably from about 0.5 to 200 mg/kg body weight and may be divided into 1 to 3 portions to take.

The pharmaceutical composition of the present invention can be prepared in various forms by customarily practical methods. In this regard, the composition may be formulated using additives acceptable for use in medicines, such as carriers or excipients for standard formulations. To improve the bioavailability or stability of the compound of the present invention, a drug delivery system including a formulation technique such as microcapsule, micronization, and clathration using cyclodextrin etc. can be used.

When the composition is used as a formulation for oral administration, the composition may take the form of, for example, a tablet, a granule, a capsule, or a liquid for oral administration, but it is preferably used in a form suitable for adsorption into the gastrointestinal tract. A conventional formulation technique can also be used when the formulation is provided in a desired form in terms of distributivity and preservability. When the composition is used as an agent for parenteral administration, the formulation can be in the form of an injection, a suppository, and a percutaneous absorption agent, such as a tape and a cataplasm. Alternatively, the formulation may take a form that can be used after dissolving a solid formulation in an appropriate solvent at the time of use for the sake of distributivity and preservability, or can be provided in a form of a liquid or a semi-solid formulation according to a conventional formulation technique.

Another aspect of the present invention pertains to a food composition comprising a hydroquinone derivative of General Formula 1 as an active ingredient.

The food composition of the present invention can be used in any form including a form of a supplement such as a tablet, a capsule, a granule and a syrup, a beverage, confectionery, a bread, rice gruel, a cereal, a noodle, a jelly, a soup, a dairy product, a flavoring, and an edible oil. When the composition is used as a food composition, other active ingredients, nutrients etc. such as a vitamin, a mineral, or an amino acid, etc. can be variously combined with the composition to the extent that they do not affect the potency of the active ingredient of the present invention. The foods obtained from the food composition of the present invention include a supplement, a health food, a functional food, and a specified health food etc. The amount of intake of the food composition of the present invention is preferably about 0.1 to 500 mg/kg body weight and is more preferably about 0.5 to 200 mg/kg body weight in terms of the hydroquinone derivative described above, and the amount is preferably divided into 1 to 3 portions for consumption.

Advantageous Effects

The composition of the present invention is a pharmaceutical composition comprising a hydroquinone derivative of General Formula 1 as an active ingredient to inhibit visceral fat accumulation and to prevent, alleviate, or treat obesity.

In addition, the composition of the present invention can suppress fat accumulation in liver tissues and treat lobular inflammation as well as reducing insulin resistance to exhibit a prophylactic, alleviative, or therapeutic effect on nonalcoholic fatty liver or NASH.

MODE FOR CARRYING OUT THE INVENTION

Figure 1:
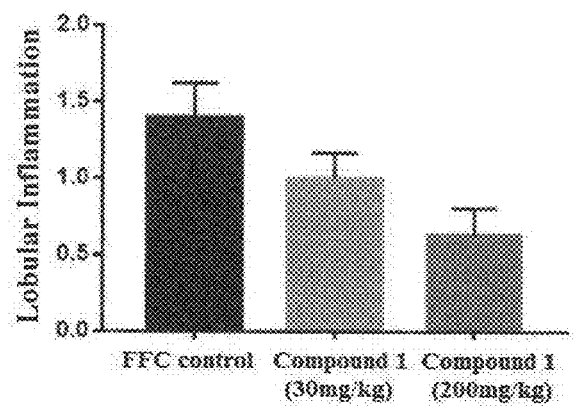
FIG. 1 is a view showing the action of compound 1 of the present invention on lobular inflammation in fat-, fructose- and cholesterol-rich (FFC) diet-fed models.

Hereinafter, preferred embodiments of the present invention will be described in detail. However, the present invention is not limited to the embodiments described herein, but may be embodied in other forms. Rather, the disclosure is thorough and complete, and is provided to enable those skilled in the art to fully understand the spirit of the invention.

[Test Example 1] Efficacy Assessment in Fat-, Fructose- and Cholesterol-Rich (FFC) Diet-Fed Non-Alcoholic Steatohepatitis Model (1) Assay Method FFC diet (fat-, fructose-, and cholesterol-rich diet) (RESEARCH DIETS, Product No.: D12079B) was fed to male C57BL/6 mice 6-7 weeks old for 16 weeks to induce nonalcoholic fatty liver. Only animals with a NAFLD activity score (NAS) of 3.2 or more were selected by biopsy. Two weeks after biopsy, the animals were divided into three test groups including a negative control injected with a 0.5% methyl cellulose (MC) aqueous solution only (FFC control) and compound 1 groups injected with a solution of compound 1 (2,3,5-trimethylhydroquinone-1-hexylether compound, 30 mg/kg and 200 mg/kg) in a 0.5% MC aqueous solution. Compound 1 was administered for a total of 2 months and evaluated for alleviative efficacy for NASH by histopathological examination.

(2) Histopathological Examination Method and Result

For histopathological examination, the mice were sacrificed and subjected to hepatectomy. The liver tissues thus obtained were prepared into hematoxylin-eosin (H&E) stained slides. In brief, the resected liver tissues were fixed in 4% paraformaldehyde at 4° C. for 24 hours, washed with flowing water, embedded into paraffin, and sectioned into blocks 3-4 μm thick. The sectioned tissue was attached to a coated slide, de-paraffinized with xylene, and rehydrated with graded alcohols (99%, 95%, 90%, 80%, and 70% ethanol (EtOH)) before histological staining. The sectioned tissues were stained with hematoxylin for 5 min and washed with flowing water for 5 min, following by destaining with 1% HCl alcohol and ammonia. Subsequently, the tissues were washed with flowing water for 10 min, counterstained with eosin for 1 min, and dehydrated in the reverse order of the hydration before mounting.

The H&E-stained slides were histopathologically assessed under a microscope and scored according to the NAFLD activity score (NAS) criteria given in Table 1.

NAFLD activity scores are expressed as a sum of assessment scores for changes in 1) steatosis, 2) lesions such as hepatic lobular inflammation, etc. (lobular inflammation), and 3) ballooning degeneration of hepatocytes (ballooning) and are widely used for evaluating the severity of NASH.

TABLE 1

Histopathological criteria for NAS (NAFLD activity score)

| Item | Definition | | Score |
|---|---|---|---|
| Steatosis | Low to medium power evaluation of parenchymal involvement by steatosis | | |
| | | <5% | 0 |
| | | 5-33% | 1 |
| | | >33-66% | 2 |
| | | >66% | 3 |
| Lobular inflammation | Overall assessment of all inflammatory foci | | |
| | | No foci | 0 |
| | | <2 foci per 200 × field | 1 |
| | | 2-4 foci per 200 × field | 2 |
| | | >4 foci per 200 × field | 3 |
| Ballooning | | None | 0 |
| | | Few balloon cells | 1 |
| | | Many cells/prominent ballooning | 2 |

Figure 2:
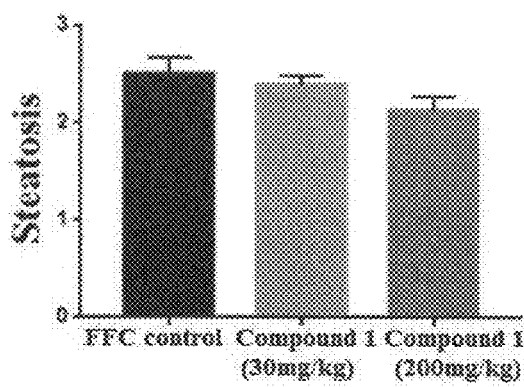
FIG. 2 is a view showing the action of compound 1 on fatty liver in FFC diet-fed models.
Figure 3:
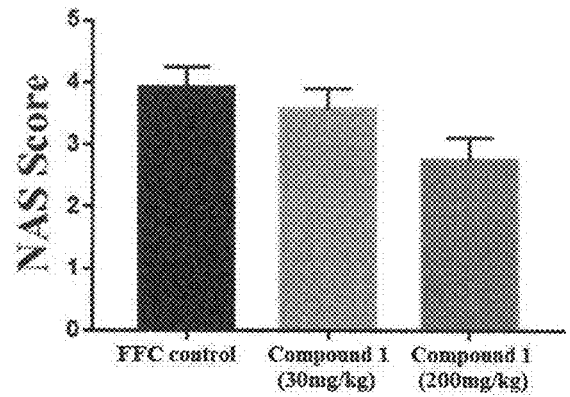
FIG. 3 is a view showing the action of compound 1 on NAFLD activity scores in FFC diet-fed models.

As shown in FIG. 1, the compound 1-administered groups were observed to decrease lobular inflammatory cellular infiltration to exhibit an excellent effect of alleviating inflammation, compared to the negative group injected with the excipient 0.5% methyl cellulose (MC) aqueous solution (FFC control) alone. In addition, compound 1 alleviated fatty liver (FIG. 2) and NAFLD activity scores (FIG. 3) in a dose-dependent manner.

Therefore, the present invention was found to have an excellent effect on the prevention or treatment of NASH.

[Test Example 2] Efficacy Assessment in NASH Model Fed with Methionine and Choline Deficient (MCD) Diet for 8 and 12 Weeks A methionine and choline deficient (MCD) diet-fed model, in which steatosis has been induced as a result of the supply of a diet deficient in methionine and choline, which each play an important role in beta oxidation and very low-density lipoprotein, (VLDL) synthesis, is widely used as a model for observing an effect of alleviating NASH because it suffers from histopathologically serious lobular inflammation.

(1) Assay Method
① Assay of Feeding MCD Diet for 8 Weeks

An MCD diet (RESEARCH DIETS, Product No: A02082002B) was fed 7-week-old male C57BL/6 mice for 4 weeks to induce nonalcoholic fatty liver and then for an additional 4 weeks during which the hydroquinone derivative compound 2,3,5-trimethylhydroquinone-1-hexylether (compound 1) according to the present invention and the comparative control drugs were orally administered to the mice at the specific doses repeatedly as indicated for test groups G3-G8 in Table 2. Alleviative effects on NASH were assessed by clinicopathological and histopathological examinations.

TABLE 2

Test Groups and Doses for MCD-fed Nonalcoholic Steatohepatitis Models

| | Test Group | | Daily dose (mg/kg) |
|---|---|---|---|
| G1 | Normal group (Normal) | | 0 |
| G2 | Negative control (MCD control) | | 0 |
| G3 | Compound 1 (2,3,5-trimethylhydroquinone-1-hexylether) | | 30 |
| G4 | Compound 1 (2,3,5-trimethylhydroquinone-1-hexylether) | | 200 |
| G5 | Comparative | Obeticholic acid (OCA) | 30 |
| G6 | group | Pioglitazone (PGZ) | 10 |
| G7 | | Resveratrol (RSV) | 200 |
| G8 | | DDB hepatoprotectant (DDB complex) | 200 |

The normal group was fed with a normal diet (RESEARCH DIETS, Product No: A02082003B), but not the MCD diet. To the negative control, only the excipient 0.5% methyl cellulose (MC) aqueous solution was administered after the MCD diet was fed thereto. For efficacy comparison assays, the FXR agonist obeticholic acid (OCA), the PPARγ agonist pioglitazone (PGZ), the antioxidant resveratrol (RSV), and the biphenyl dimethyl dicarboxylate (DDB) hepatoprotectant (DDB complex) were administered to the comparative controls as suggested in Table 2. For resveratrol and the DDB hepatoprotectant, the daily dose was set forth to be 200 mg/kg. Daily doses of obeticholic acid and pioglitazone were determined to be 30 mg/kg/day and 10 mg/kg, respectively as shown in Table 2, with reference to toxicity doses detected through approval data from the FDA and the EMA and effective doses and side effect doses reported in articles.

For obeticholic acid, a toxicity assay in which CD-1(ICR) mice were repeatedly administered for 7 days (doses of 3, 50, 175, and 300 mg/kg) reported that serious side effects such as death of animals were caused at a dose of 175 mg/kg or higher (FDA obeticholic acid (INT-747) NDA package pharmacology reviews; Application number: 207999Orig1s000). In addition, an efficacy assay in western diet NASH mouse models reported that a dose of 40 mg/kg or higher aggravated NAFLD (liver fibrosis worsen, ALT level increased) rather (Front Pharmacol. 2018 May 1; 9:410). Accordingly, in the dose range of 20-30 mg/kg, which had been adopted in many research articles for nonalcoholic fatty liver in mice, the maximum dose 30 mg/kg was determined as a test dose.

For pioglitazone, a toxicity assay where mice were administered repeatedly for 13 weeks reported subject death occurred at a dose of 320 mg/kg or greater and cardiac adverse effects at a dose of 100 mg/kg or greater (FDA Pioglitazone (ACTOS) NDA package pharmacology reviews: 021073). In addition, research articles employed 10-30 mg/kg as an effective dose range for nonalcoholic fatty liver in mice, but there is a research result that a pioglitazone dose of 25 mg/kg rather aggravates fatty liver (Int. J. Mol. Sci. 2015, 16, 12213-12229, PPAR Res. 2014: 38183). With reference to such data, the most frequently reported dose 10 mg/kg was set forth as a test dose.

② Assay of Feeding MCD Diet for 12 Weeks

The duration of feeding MCD diet was extended to a total of 12 weeks to increase the induction level of NASH. To this end, male C57BL/6 mice at 7 weeks of age were fed with a methionine and choline-deficient diet for 8 weeks to induce nonalcoholic fatty liver and then subjected to the same repeat administration program at the same doses for 4 weeks as in Table 2.

(2) Histopathological and Clinicopathological Assessment Result

① Assay of Feeding MCD Diet for 8 Weeks

The liver tissues were resected from mice fed with MCD diet for 8 weeks and prepared into hematoxylin-eosin (H&E) stained slides, as in the histopathological examination method of Test Example 1. Based on the criteria of Table 1, changes in 1) steatosis, 2) lesions such as hepatic lobular inflammation, etc. (lobular inflammation), and 3) ballooning degeneration of hepatocytes (ballooning) were analyzed and the scores were summed to afford NAFLD activity scores for evaluating therapeutic effects on NASH.

Figure 4:
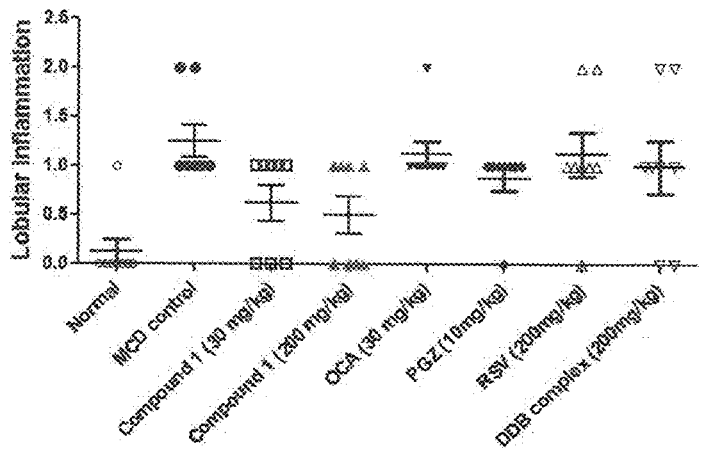
FIG. 4 is a view showing the action of compound 1 on lobular inflammation in models fed with methionine and choline deficient (MCD) diet for 8 weeks.
Figure 5:
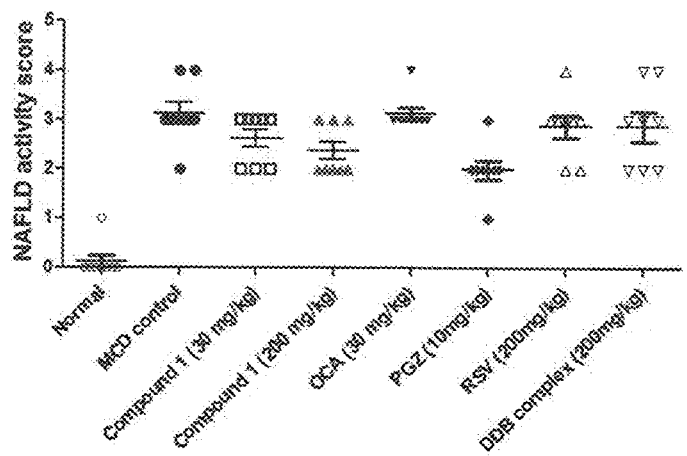
FIG. 5 is a view showing the action of compound 1 on NAFLD activity scores in models fed with MCD diet for 8 weeks.
Figure 6:
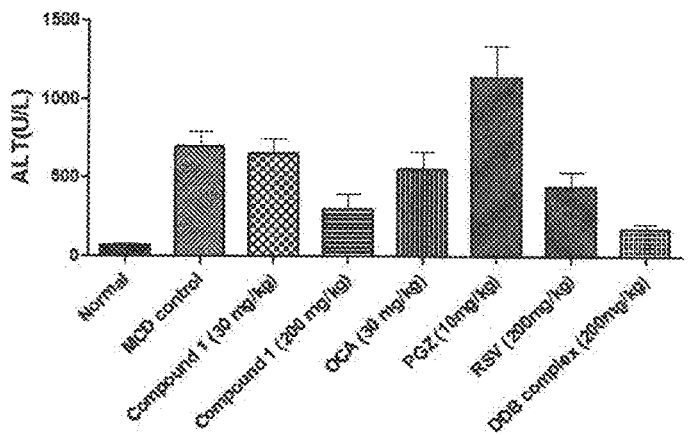
FIG. 6 is a view showing the action of compound 1 on ALT levels in models fed with MCD diet for 8 weeks.

Histopathological lobular inflammation scores and NAFLD activity scores in mouse liver tissues are depicted in FIGS. 4 and 5 and ALT levels, which representatively account for clinicopathological liver function, are given in FIG. 6.

The lobular inflammatory cellular infiltration score shown in FIG. 4 is one of the most important indices for histopathological assessment of NASH. In addition, the alleviation of histopathological lobular inflammation is a very important efficacy factor in that the most goal of drug treatment for NASH is to prevent progression to a subsequent aggravated phase such as from fatty liver to steatohepatitis or from steatohepatitis to liver cirrhosis.

The effect of reducing lobular inflammatory cellular infiltration was remarkable in the compound 1-administered groups, compared to the negative control (MCD control) (FIG. 4). Particularly, compound 1 of the present invention exhibited excellent anti-inflammatory efficacy, compared to pioglitazone (PGZ), which is an insulin resistance-reducing drug for current clinical use as a primary therapeutic agent for NASH, and obeticholic acid (OCA), which is currently under clinical phase III.

In addition, compound 1 of the present invention was observed to reduce NAFLD activity scores (FIG. 5). Also, an ALT level, which is a clinicopathological index for liver function, was remarkably reduced in the group administered compound 1 at a dose of 200 mg/kg, compared to the negative control and the comparative control groups (FIG. 6).

Resveratrol (RSV) and DDB hepatoprotectant (DDB complex), which are known to have antioxidant and anti-inflammatory effects, did not exhibit an alleviative effect on NASH, compared to the negative control. This implicates that NASH, which has a complicated pathological mechanism, cannot be inhibited by general antioxidant or anti-inflammatory effects alone. On the basis of the data, compound 1 of the present invention was found to have excellent inhibitory activity against NASH, compared to a group of drugs of various acting mechanisms under development for treating NASH.

② Assay of Feeding MCD Diet for 12 Weeks

Figure 7:
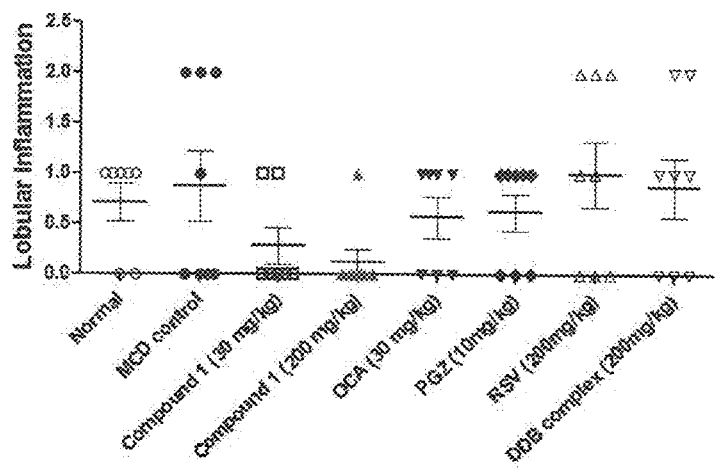
FIG. 7 is a view showing the action of compound 1 on lobular inflammation in models fed with MCD diet for 12 weeks.
Figure 8:
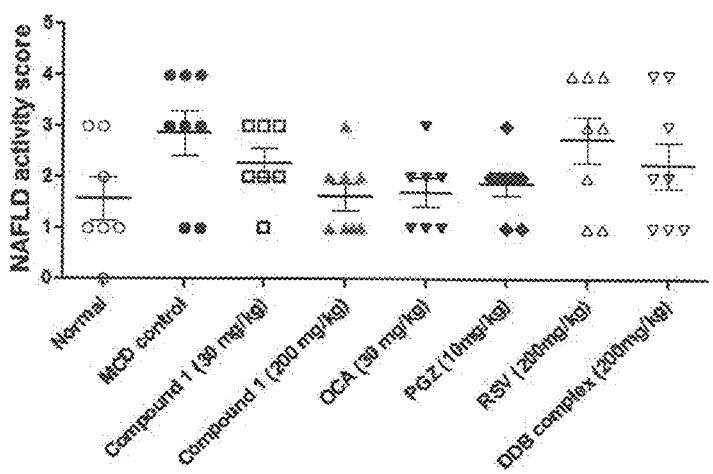
FIG. 8 is a view showing the action of compound 1 on NAFLD activity scores in models fed with MCD diet for 12 weeks.

Effects of alleviating lobular inflammatory cellular infiltration and NAFLD activity scores in liver tissues from mice fed with MCD diet for 12 weeks are depicted in FIGS. 7 and 8.

As can be seen in FIGS. 7 and 8, the compound 1-administered groups suffered from reduced lobular inflammatory cellular infiltration, with lowered NAFLD activity scores, compared to the negative control (MCD control). The effect of compound 1 was observed to increase in a dose-dependent manner. Compound 1 exhibited an excellent anti-inflammatory effect, compared particularly to pioglitazone (PGZ), which is an insulin resistance reducing agent currently used as a primary clinical therapeutic for NASH, and even to obeticholic acid (OCA), which is under development in clinical trial phase III.

Resveratrol (RSV) and DDB hepatoprotectant (DDB complex), which are known to have antioxidant and anti-inflammatory effects, did not exhibit an alleviative effect on NASH in this assay example, either, compared to the negative control. This implicates that general antioxidant or anti-inflammatory effects alone are not sufficient to inhibit NASH, which has a complicated pathological mechanism.

[Test Example 3] Efficacy Assessment in Obesity and NASH Model Fed with High-Fat Diet (HFD)

(1) Assay Method

High-fat diet with 60 kcal % (RESEARCH DIETS, Product No: D12492) was fed to 7-week-old male C57BL/6 mice for 16 weeks to induce nonalcoholic fatty liver, followed by repeatedly administering test substances, along with the high-fat diet, via an oral route for 9 weeks from weeks 17 to 25. Alleviative effects on NASH were assessed by clinicopathological and histopathological examinations.

The test groups included a normal control which was not fed with HFD, but with a normal diet (10 kcal % fat diet, RESEARCH DIETS, Product No: D12450B), a negative control which was fed with HFD and then with the excipient 0.5% methyl cellulose (MC) aqueous solution alone, compound 1 (2,3,5-trimethylhydroquinone-1-hexylether)-administered groups (30, 100, 200 mg/kg), and comparative controls (obeticholic acid 30 mg/kg, pioglitazone 10 mg/kg, and DDB hepatoprotectant 200 mg/kg).

(2) Inhibitory Effect on Weight Gain and Visceral Fat Accumulation

During repeatedly oral administration of the test substances for 9 weeks as in the assay method of (1), the mice were observed and recorded for weight gain, food intake, and general symptoms.

Figure 9:
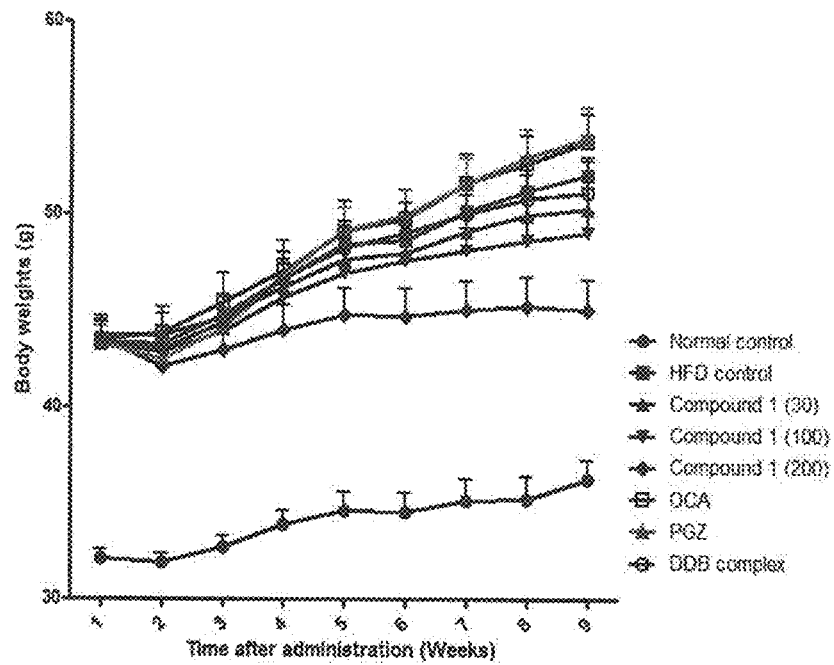
FIG. 9 is a view showing the action of compound 1 on body weights in high-fat diet-fed models.
Figure 10:
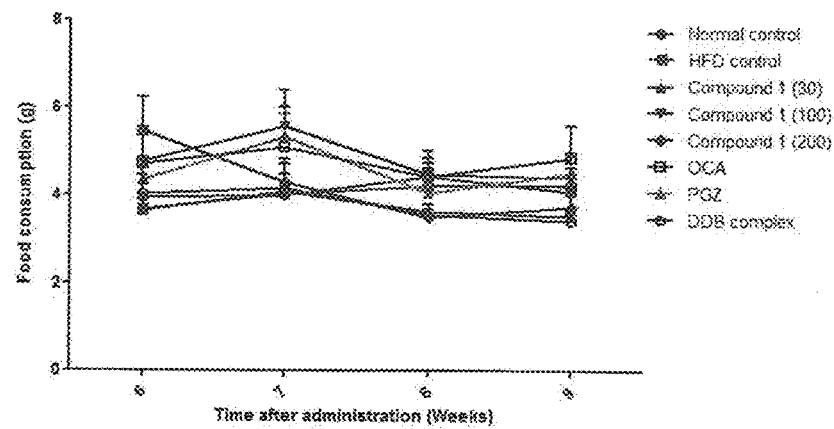
FIG. 10 is a view showing the action of compound 1 on food intake in high-fat diet-fed models.

As can be seen in FIG. 9, weight gain increments resulting from the intake of high-fat diet were remarkably reduced in the compound 1-administered groups, compared to the negative control (HFD control). Particularly, the compound 1-administered groups were not different in food intake from the other groups (FIG. 10), which implies that the weight gain decrease of the compound 1-administered groups was not attributed to lowered food consumption.

Figure 11:
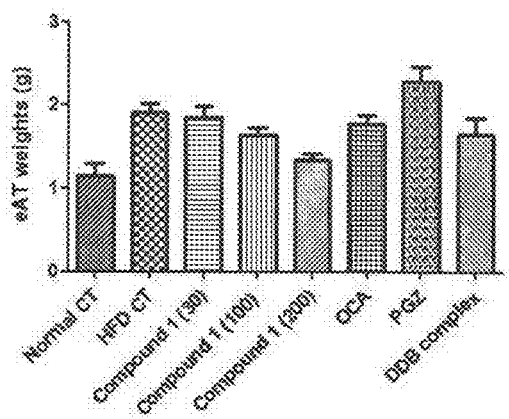
FIG. 11 is a view showing the action of compound 1 on epididymal fat weights in high-fat diet-fed models.

In addition, the mice were autopsied and the epididymal fats were measured. As shown in FIG. 11, compound 1 had an excellent effect of inhibiting the accumulation of visceral fats such as epididymal fats. Such visceral fats as epididymal fats are known to have close correlation with the progression and prognosis of NASH because visceral fats are recruited faster than subcutaneous fats and directly introduced into the liver through the hepatic portal vein to cause liver injury.

Like this, compound 1 was found to have an excellent effect of reducing body weight and visceral fat, thereby finding effective applications in preventing, alleviating, or treating obesity.

Figure 12:
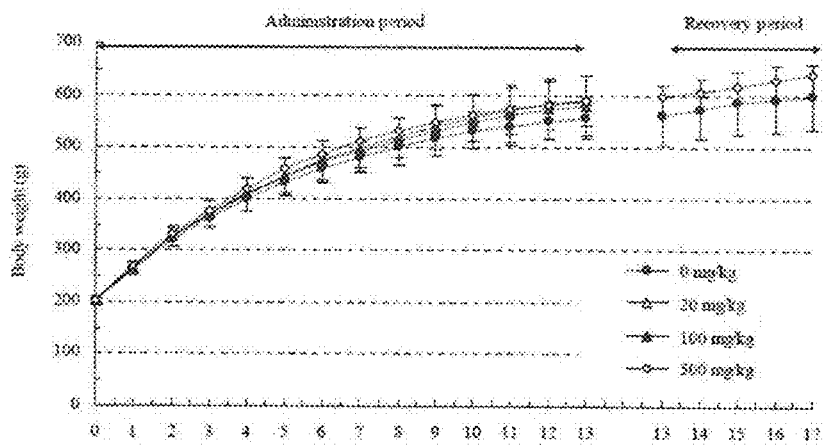
FIG. 12 is a view showing changes in body weight over 13 weeks for repetitive toxicity examination according to daily doses of compound 1.

Furthermore, compound 1 did not cause mortality even at a dose of as high as 2000 mg/kg in the groups, as analyzed by a single-dose oral administration assay for rats, as opposed to other drugs which target metabolic pathways leading to a side effect even in normal animals. In addition, even after a toxicity assay in which a dose of as high as 500 mg/kg was repeatedly administered via an oral route for 13 weeks, compound 1 did not invoke significant side effects such as death, organ failure, etc. No changes attributed to the administration of compound 1 were detected for weight gain (FIG. 12) and food consumption and from urological and serological examinations.

(3) Reductive Effect on Insulin Resistance

An insulin resistance assay was conducted on week 7 of administration of compound 1 to examine the effect of compound 1 on the insulin resistance induced by high-fat diet.

Figure 14:
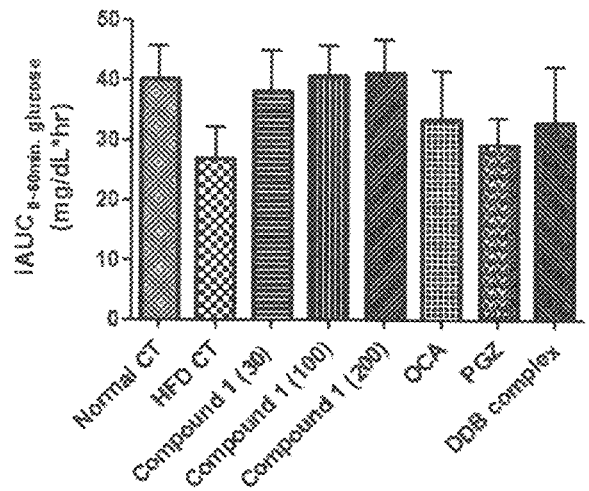
FIG. 14 is a view showing an increase in sensitivity to insulin in response to treatment with compound 1, as expressed by iAUC values digitized from results of insulin resistance examination.

For the insulin resistance assay, the mice were fast for 4 hours and intraperitoneally injected with insulin (0.7 IU/kg), followed by measuring blood glucose levels every 30 min. Insulin resistance was digitized for quantitative comparison. In this regard, while pre-insulin blood levels were set forth to be baselines, areas under the curves of reduced blood glucose levels were digitized into iAUC values (FIG. 14). Here, a smaller iAUC value means higher insulin resistance and a larger iAUC value means higher insulin sensitivity.

Figure 13:
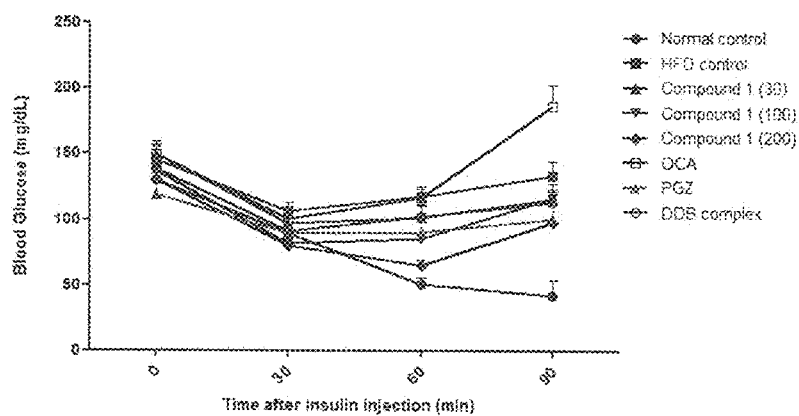
FIG. 13 is a view showing changes in blood glucose level with time for insulin resistance examination.

From the insulin resistance assay, it was observed that, as shown in FIG. 13, the compound 1-administered group reduced in blood glucose level more fast than the negative control and the other drug controls upon insulin administration. For the negative control, the blood glucose level was slowly reduced due to an increase of insulin resistance in peripheral tissues. When administered, however, compound 1 was observed to increase sensitivity to insulin and thus decrease the blood glucose level quickly. As shown in FIG. 14 where digitized iAUC values are given, compound 1 was also demonstrated to have a higher suppressive effect on high-fat diet-induced insulin resistance, compared to the negative control and the other drug controls.

(4) Histopathological and Clinicopathological Assessment Result

Liver tissues were resected from HFD-fed mice and prepared into hematoxylin-eosin (H&E) stained slides, as in the histopathological examination method of Test Example 1. Based on the criteria of Table 1, changes in 1) steatosis, 2) lesions such as hepatic lobular inflammation, etc. (lobular inflammation), and 3) ballooning degeneration of hepatocytes (ballooning) were analyzed and the scores were summed to afford NAFLD activity scores for evaluating therapeutic effects on NASH.

Figure 15:
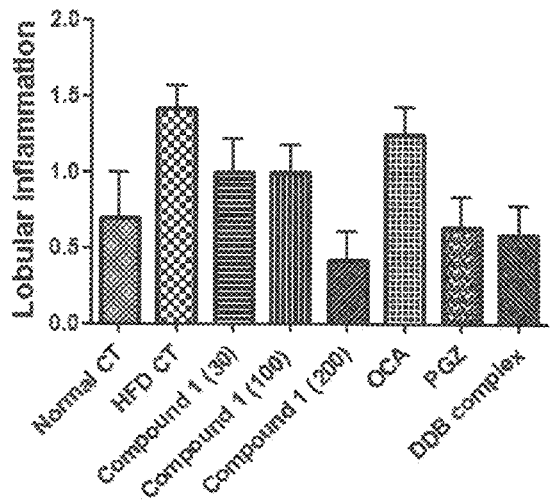
FIG. 15 is a view showing the action of compound 1 on lobular inflammation in high-fat diet-fed models.
Figure 16:
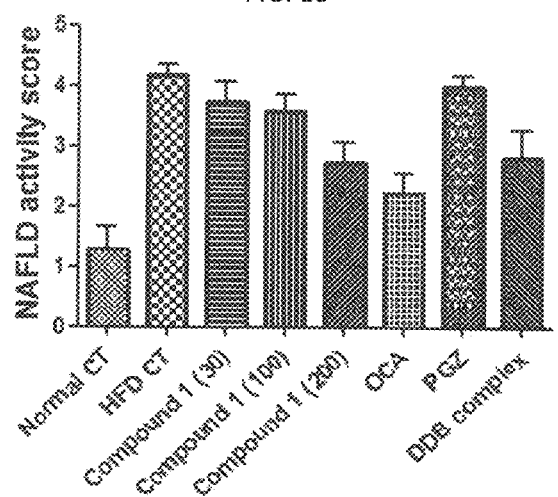
FIG. 16 is a view showing the action of compound 1 on NAFLD activity scores in high-fat diet-fed models.

FIGS. 15 and 16 shows results of the histopathological examinations in which compound 1 has excellent therapeutic effects on NASH, compared to the other drugs. As can be seen in FIGS. 15 and 16, compound 1 alleviated hepatic lobular cellular infiltration and fatty liver, compared to the negative control (HFD control). The alleviative effect of compound 1 increased in a dose-dependent manner. Moreover, a remarkably highly suppressive effect on lobular inflammation was detected in the group to which compound 1 had been administered at a dose of 200 mg/kg, compared to the other drug groups.

Figure 17:
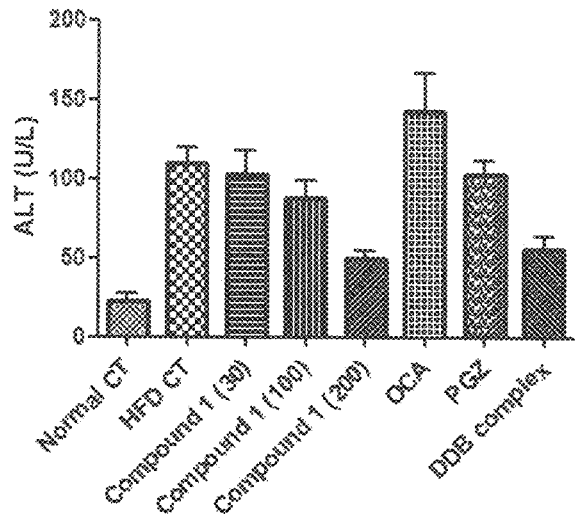
FIG. 17 is a view showing the action of compound 1 on ALT levels in high-fat diet-fed models.
Figure 18:
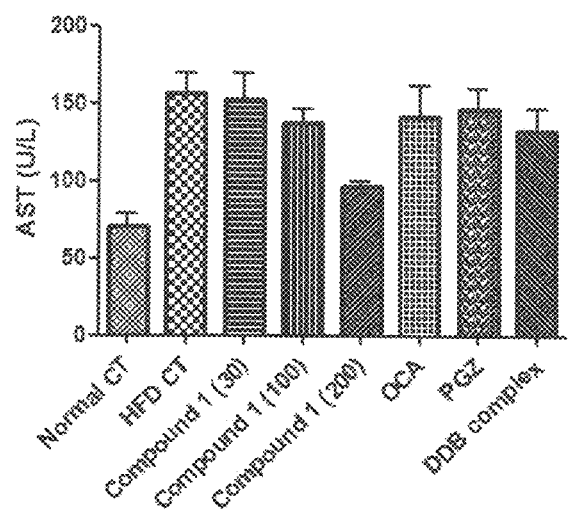
FIG. 18 is a view showing the action of compound 1 on AST levels in high-fat diet-fed models.

The clinicopathological examination also showed that the administration of compound 1 recovered ALT and AST, which are indices for liver function and injury, to normal levels. Particularly, ALT and AST levels were further reduced by compound 1 than the other drug controls (FIGS. 17 and 18).

Figure 19:
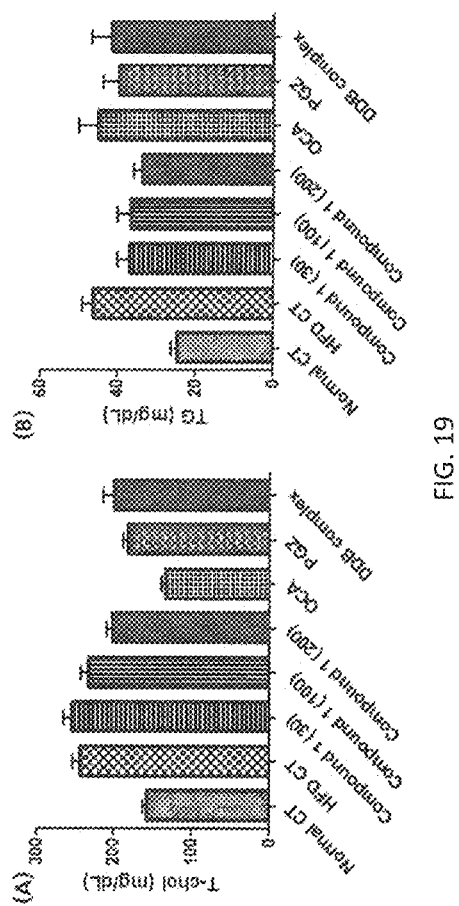
FIG. 19 is a view showing the action of compound 1 on blood cholesterol levels (A) and blood triglyceride levels (TG) in high-fat diet-fed models.

Moreover, blood levels of cholesterol and triglyceride, which aggravate progression into fatty liver and steatohepatitis, were reduced in the compound 1-administered groups, compared to the negative control (FIGS. 19(A) and (B)). Obeticholic acid, although exhibiting a high suppressive action on cholesterol in the animal assay, is known to have the side effect of increasing total cholesterol and LDL cholesterol levels in both normal persons and nonalcoholic fatty liver patients even at low doses (10-25 mg per adult) as analyzed by clinical examination (Diabetes, Obesity and Metabolism 18: 936-940, 2016). In contrast, no abnormal responses, such as dyslipidemia, were reported even after compound 1 of the present invention was repetitively administered at a dose of 1000 mg per adult for 14 days for clinical trial phase I.

(5) Comprehensive Evaluation

Identified to have excellent alleviative effects on weight gain and visceral fat accumulation as measured by high-fat diet-fed animal model assays, compound 1 of the present invention can find advantageous applications as an agent for prevention, alleviation, or treatment of obesity.

In addition, compound 1 of the present invention was found to highly effectively suppress weight gain and visceral fat accumulation, increase sensitivity to insulin and inhibit lobular inflammation, compared to conventionally developed therapeutics for NASH, and thus is very effective for treatment of NASH in which complicated and various factors are involved.

Furthermore, compound 1 of the present invention was identified as a very safe compound with a lethal dose for 50% kill of 2,000 mg/kg in rats and a maximum tolerance dose of 2,000 mg/kg in beagle dogs. In the toxicity assay of repetitive administration for 13 weeks to rats, no side effects such as death, weight loss, organ failure, etc. were detected even at a dose of as high as 500 mg/kg. In addition, compound 1 was proven to be safe through clinical trial phase 1 in which no abnormal responses were observed even at a single dose of up to 2,000 mg per adult and at a dose of up to 1,000 mg per adult for repetitive administration for 14 days and thus can be advantageously used as a therapeutic for NASH, which needs a long-term care.

The invention claimed is:

1. A method for treating obesity or nonalcoholic steatohepatitis, comprising administering to a subject in need thereof a therapeutically effective amount of a pharmaceutical composition comprising 2,3,5-trimethylhydroquinone-1-hexylether or 2,3,5-trimethylhydroquinone-1-hexylether-4-acetate.

\* \* \* \* \*